(12) United States Patent  
Berzak et al.

(10) Patent No.: US 7,967,815 B1
(45) Date of Patent: Jun. 28, 2011

(54) CRYOSURGICAL INSTRUMENT WITH ENHANCED HEAT TRANSFER

(75) Inventors: Nir Berzak, Givataim (IL); Simon Sharon, Ma'ayan Zvi (IL); Igal Shteiman, Afula (IL); Eytan Shilder, Ramat Gan (IL)

(73) Assignee: IceCure Medical Ltd., Caesarea (IL)

( * ) Notice: Subject to any disclaimer, the term of this patent is extended or adjusted under 35 U.S.C. 154(b) by 0 days.

(21) Appl. No.: 12/731,219

(22) Filed: Mar. 25, 2010

(51) Int. Cl.
*A61B 18/02* (2006.01)
(52) U.S. Cl. .......................... 606/23; 606/22
(58) Field of Classification Search ........... 606/20–26
See application file for complete search history.

(56) References Cited

U.S. PATENT DOCUMENTS

| | | |
|---|---|---|
| 3,234,746 A | 2/1966 | Smith |
| 3,358,472 A | 12/1967 | Kipling |
| 3,664,344 A | 5/1972 | Bryne |
| 3,699,775 A | 10/1972 | Cowans |
| 3,712,306 A | 1/1973 | Bryne |
| 3,736,936 A | 6/1973 | Basiulis |
| 3,736,937 A * | 6/1973 | Basiulis .......................... 606/23 |
| 3,800,552 A | 4/1974 | Sollami |
| 3,862,630 A | 1/1975 | Balamuth |
| 3,882,849 A | 5/1975 | Jamshidi |
| 3,938,505 A | 2/1976 | Jamshidi |
| 3,971,383 A | 7/1976 | Van Gerven |
| 4,082,096 A | 4/1978 | Benson |
| 4,091,634 A | 5/1978 | Shepherd |
| 4,127,903 A | 12/1978 | Schachar |
| 4,200,104 A | 4/1980 | Harris |
| 4,202,336 A * | 5/1980 | van Gerven .................. 606/21 |
| 4,211,231 A | 7/1980 | Rzasa |
| 4,279,626 A | 7/1981 | Buchmuller |
| 4,306,568 A | 12/1981 | Torre |
| 4,313,306 A | 2/1982 | Torre |
| 4,367,744 A | 1/1983 | Sole |
| 4,428,748 A | 1/1984 | Peyman |
| 4,463,458 A | 8/1984 | Seidner |
| 4,481,948 A | 11/1984 | Sole |
| 4,487,253 A | 12/1984 | Malek |
| 4,552,208 A | 11/1985 | Sorensen |
| 4,570,626 A | 2/1986 | Norris |
| 4,573,525 A | 3/1986 | Boyd |
| 4,611,654 A | 9/1986 | Buchsel |

(Continued)

FOREIGN PATENT DOCUMENTS

CA 2437079 6/2004

(Continued)

OTHER PUBLICATIONS

Verkin et al., Low Temperatures in Stomatology, Naukova Dumka, 1990, pp. 62-63, Kiev.

(Continued)

*Primary Examiner* — Michael Peffley
(74) *Attorney, Agent, or Firm* — The Law Office of Michael E. Kondoudis

(57) ABSTRACT

Cryosurgical instruments and methods utilizing improved heat transfer characteristics. A cryosurgical device includes: a tubular housing; a cryogen supply passage; a heat exchange enhancing member in the housing, disposed along a longitudinal axis of the housing; an annular cooling passage between the heat exchange enhancing member and the tubular housing; a tip cooling and cryogen flow directing section that transmits a temperature of a cryogen flow to the tip, and an insulation element in the tubular housing.

6 Claims, 14 Drawing Sheets

U.S. PATENT DOCUMENTS

| | | | |
|---|---|---|---|
| 4,617,018 A | 10/1986 | Nishi | |
| 4,676,225 A | 6/1987 | Bartera | |
| 4,726,194 A | 2/1988 | Mackay | |
| 4,765,396 A | 8/1988 | Seidenberg | |
| 4,770,171 A | 9/1988 | Sweren | |
| 4,802,475 A | 2/1989 | Weshahy | |
| 4,831,856 A | 5/1989 | Gano | |
| 4,946,460 A | 8/1990 | Merry | |
| 5,026,387 A | 6/1991 | Thomas | |
| 5,047,043 A | 9/1991 | Kubota | |
| 5,108,390 A | 4/1992 | Potocky | |
| 5,147,355 A | 9/1992 | Friedman | |
| 5,188,102 A | 2/1993 | Idemoto | |
| 5,214,925 A | 6/1993 | Hoy | |
| 5,222,937 A | 6/1993 | Kagawa | |
| 5,224,943 A | 7/1993 | Goddard | |
| 5,243,826 A | 9/1993 | Longsworth | |
| 5,254,082 A | 10/1993 | Takase | |
| 5,254,116 A | 10/1993 | Baust | |
| 5,261,923 A | 11/1993 | Soares | |
| 5,263,957 A | 11/1993 | Davison | |
| 5,264,116 A | 11/1993 | Apelian | |
| 5,275,595 A | 1/1994 | Dobak | |
| 5,281,215 A | 1/1994 | Milder | |
| 5,295,484 A | 3/1994 | Marcus | |
| 5,324,286 A | 6/1994 | Fowle | |
| 5,330,745 A | 7/1994 | Mcdow | |
| 5,334,181 A | 8/1994 | Rubinsky | |
| 5,342,380 A | 8/1994 | Hood | |
| 5,361,591 A | 11/1994 | Caldwell | |
| 5,391,144 A | 2/1995 | Sakurai | |
| 5,411,374 A | 5/1995 | Gram | |
| 5,417,073 A | 5/1995 | James | |
| 5,423,807 A | 6/1995 | Milder | |
| 5,429,138 A | 7/1995 | Jamshidi | |
| 5,438,837 A | 8/1995 | Caldwell | |
| 5,441,512 A | 8/1995 | Muller | |
| 5,445,462 A | 8/1995 | Johnson | |
| 5,452,582 A | 9/1995 | Longsworth | |
| 5,488,831 A | 2/1996 | Griswold | |
| 5,516,505 A | 5/1996 | Mcdow | |
| 5,520,682 A | 5/1996 | Baust | |
| 5,526,821 A | 6/1996 | Jamshidi | |
| 5,547,473 A | 8/1996 | Peyman | |
| 5,573,532 A | 11/1996 | Chang | |
| 5,600,143 A | 2/1997 | Roberts | |
| 5,647,868 A | 7/1997 | Chinn | |
| 5,654,279 A | 8/1997 | Rubinsky | |
| 5,658,276 A | 8/1997 | Griswold | |
| 5,674,218 A | 10/1997 | Rubinsky | |
| 5,683,592 A | 11/1997 | Bartholomew et al. | |
| 5,687,776 A | 11/1997 | Forgash | |
| 5,716,353 A | 2/1998 | Matsuura | |
| 5,720,743 A | 2/1998 | Bischof | |
| 5,728,130 A | 3/1998 | Ishikawa | |
| 5,735,845 A | 4/1998 | Zupkas | |
| 5,771,946 A | 6/1998 | Kooy | |
| 5,787,940 A | 8/1998 | Bonn | |
| 5,800,448 A | 9/1998 | Banko | |
| 5,800,487 A | 9/1998 | Mikus | |
| 5,814,040 A | 9/1998 | Nelson | |
| 5,860,970 A * | 1/1999 | Goddard et al. | 606/23 |
| 5,868,673 A | 2/1999 | Vesely | |
| 5,885,276 A | 3/1999 | Ammar | |
| 5,899,897 A | 5/1999 | Rabin | |
| 5,906,612 A | 5/1999 | Chinn | |
| 5,906,628 A | 5/1999 | Miyawaki | |
| 5,910,104 A | 6/1999 | Dobak | |
| 5,921,982 A | 7/1999 | Lesh | |
| 5,976,092 A | 11/1999 | Chinn | |
| 5,976,505 A | 11/1999 | Henderson | |
| 5,992,158 A | 11/1999 | Goddard | |
| 6,012,453 A | 1/2000 | Tsais | |
| 6,024,750 A | 2/2000 | Mastri | |
| 6,027,499 A | 2/2000 | Johnston | |
| 6,032,068 A | 2/2000 | Daniel | |
| 6,032,675 A | 3/2000 | Rubinsky | |
| 6,035,657 A | 3/2000 | Dobak | |
| 6,036,667 A | 3/2000 | Manna | |
| 6,039,730 A | 3/2000 | Rabin | |
| 6,041,787 A | 3/2000 | Rubinsky | |
| 6,042,342 A | 3/2000 | Orian | |
| 6,053,906 A | 4/2000 | Honda | |
| 6,059,820 A | 5/2000 | Baronov | |
| 6,063,098 A | 5/2000 | Houser | |
| 6,095,149 A | 8/2000 | Sharkey | |
| 6,142,991 A | 11/2000 | Schatzberger | |
| 6,152,894 A | 11/2000 | Kubler | |
| 6,182,666 B1 | 2/2001 | Dobak | |
| 6,200,308 B1 | 3/2001 | Pope | |
| 6,206,832 B1 | 3/2001 | Downey | |
| 6,212,904 B1 | 4/2001 | Arkharov | |
| 6,216,029 B1 | 4/2001 | Paltieli | |
| 6,235,018 B1 | 5/2001 | LePivert | |
| 6,237,355 B1 | 5/2001 | Li | |
| 6,251,105 B1 | 6/2001 | Mikus | |
| 6,270,494 B1 | 8/2001 | Kovalcheck | |
| 6,280,407 B1 | 8/2001 | Manna | |
| 6,354,088 B1 | 3/2002 | Emmer | |
| 6,355,033 B1 | 3/2002 | Moorman et al. | |
| 6,358,264 B2 | 3/2002 | Banko | |
| 6,379,348 B1 | 4/2002 | Onik | |
| 6,383,180 B1 | 5/2002 | Lalonde | |
| 6,383,181 B1 | 5/2002 | Johnston | |
| 6,411,852 B1 | 6/2002 | Danek | |
| 6,413,263 B1 | 7/2002 | Lobdill | |
| 6,423,009 B1 | 7/2002 | Downey | |
| 6,432,102 B2 | 8/2002 | Joye | |
| 6,457,212 B1 | 10/2002 | Craig | |
| 6,468,268 B1 | 10/2002 | Abboud | |
| 6,468,269 B1 | 10/2002 | Korpan | |
| 6,471,217 B1 | 10/2002 | Hayfield | |
| 6,482,178 B1 | 11/2002 | Andrews | |
| 6,497,714 B1 | 12/2002 | Ishikawa | |
| 6,500,109 B2 | 12/2002 | Tokita | |
| 6,503,246 B1 | 1/2003 | Har-Shai | |
| 6,508,814 B2 | 1/2003 | Tortal | |
| 6,513,336 B2 | 2/2003 | Zurecki | |
| 6,547,784 B1 | 4/2003 | Thompson | |
| 6,551,309 B1 | 4/2003 | LePivert | |
| 6,562,030 B1 | 5/2003 | Abboud | |
| 6,565,556 B1 | 5/2003 | Korpan | |
| 6,581,390 B2 | 6/2003 | Emmer | |
| 6,582,426 B2 | 6/2003 | Moorman | |
| 6,631,615 B2 | 10/2003 | Drube | |
| 6,640,556 B2 | 11/2003 | Ursan | |
| 6,659,730 B2 | 12/2003 | Gram | |
| 6,659,956 B2 | 12/2003 | Barzell et al. | |
| 6,672,095 B1 | 1/2004 | Luo | |
| 6,678,621 B2 | 1/2004 | Wiener | |
| 6,682,525 B2 | 1/2004 | Lalonde | |
| 6,698,423 B1 | 3/2004 | Honkonen | |
| 6,702,761 B1 | 3/2004 | Damadian | |
| 6,761,715 B2 | 7/2004 | Carroll | |
| 6,765,333 B1 | 7/2004 | Mariaucue | |
| 6,768,917 B1 | 7/2004 | Van Vaals | |
| 6,772,766 B2 | 8/2004 | Gallo | |
| 6,786,902 B1 | 9/2004 | Rabin | |
| 6,824,543 B2 | 11/2004 | Lentz | |
| 6,852,706 B1 | 2/2005 | Heber-Katz | |
| 6,858,025 B2 | 2/2005 | Maurice | |
| 6,869,439 B2 | 3/2005 | White | |
| 6,889,695 B2 | 5/2005 | Pankratov | |
| 6,898,940 B2 | 5/2005 | Gram | |
| 6,908,472 B2 | 6/2005 | Wiener | |
| 6,910,510 B2 | 6/2005 | Gale | |
| 6,913,604 B2 | 7/2005 | Mihalik | |
| 6,932,771 B2 | 8/2005 | Whitmore | |
| 6,936,045 B2 | 8/2005 | Yu | |
| 6,942,659 B2 | 9/2005 | Lehmann | |
| 6,951,569 B2 | 10/2005 | Nohilly | |
| 6,954,977 B2 | 10/2005 | Maguire | |
| 6,995,493 B2 | 2/2006 | Isoda | |
| 7,001,378 B2 | 2/2006 | Yon | |
| 7,025,762 B2 | 4/2006 | Johnston | |
| 7,025,767 B2 | 4/2006 | Schaefer | |
| 7,071,690 B2 | 7/2006 | Butts | |

| | | | |
|---|---|---|---|
| 7,081,111 B2 | 7/2006 | Svaasand | |
| 7,101,367 B2 | 9/2006 | Xiao et al. | |
| 7,128,739 B2 | 10/2006 | Prakash | |
| 7,137,978 B2 | 11/2006 | Levin | |
| 7,144,228 B2 | 12/2006 | Emmer | |
| 7,151,374 B2 | 12/2006 | Doty | |
| 7,156,840 B2 * | 1/2007 | Lentz et al. | 606/21 |
| 7,160,291 B2 | 1/2007 | Damasco | |
| 7,160,292 B2 | 1/2007 | Moorman | |
| 7,165,422 B2 | 1/2007 | Little | |
| 7,189,228 B2 | 3/2007 | Eum | |
| 7,207,985 B2 | 4/2007 | Duong | |
| 7,213,400 B2 | 5/2007 | Dickerson | |
| 7,223,080 B2 | 5/2007 | Duron | |
| 7,250,046 B1 | 7/2007 | Fallat | |
| 7,252,648 B2 | 8/2007 | Honda | |
| 7,255,693 B1 | 8/2007 | Johnston | |
| 7,273,479 B2 | 9/2007 | Littrup | |
| 7,278,991 B2 | 10/2007 | Morris | |
| 7,280,623 B2 | 10/2007 | Gupta | |
| 7,282,919 B2 | 10/2007 | Doty | |
| 7,288,089 B2 | 10/2007 | Yon | |
| 7,318,327 B2 | 1/2008 | Dickerson | |
| 7,344,530 B2 | 3/2008 | Bischoff | |
| 7,344,531 B2 | 3/2008 | Bischoff | |
| 7,354,434 B2 | 4/2008 | Zvuloni | |
| 7,361,187 B2 | 4/2008 | Duong | |
| 7,381,207 B2 | 6/2008 | Duong | |
| 7,425,211 B2 | 9/2008 | Levin et al. | |
| 7,458,968 B2 | 12/2008 | Carroll | |
| 7,481,806 B2 | 1/2009 | Levin | |
| 7,485,117 B2 | 2/2009 | Damasco | |
| 7,498,812 B2 | 3/2009 | Doty | |
| 7,510,554 B2 | 3/2009 | Duong | |
| 7,563,260 B2 | 7/2009 | Whitmore | |
| 7,731,711 B2 | 6/2010 | Levin | |
| 7,803,154 B2 | 9/2010 | Toubia et al. | |
| 2001/0047129 A1 | 11/2001 | Hall | |
| 2002/0016540 A1 | 2/2002 | Mikus | |
| 2002/0022832 A1 | 2/2002 | Mikus | |
| 2002/0040220 A1 | 4/2002 | Zvuloni | |
| 2002/0077654 A1 | 6/2002 | Javier | |
| 2002/0085921 A1 | 7/2002 | Gram | |
| 2002/0144509 A1 | 10/2002 | Chalk | |
| 2002/0156469 A1 | 10/2002 | Yon | |
| 2002/0157402 A1 | 10/2002 | Drube | |
| 2002/0160640 A1 | 10/2002 | Korpan | |
| 2002/0161385 A1 | 10/2002 | Wiener | |
| 2003/0060762 A1 | 3/2003 | Zvuloni | |
| 2003/0079480 A1 | 5/2003 | Emmer | |
| 2003/0126867 A1 | 7/2003 | Drube | |
| 2003/0135119 A1 | 7/2003 | Lee | |
| 2003/0181897 A1 | 9/2003 | Thomas | |
| 2003/0220635 A1 | 11/2003 | Knowlton | |
| 2004/0024391 A1 | 2/2004 | Cytron | |
| 2004/0055316 A1 | 3/2004 | Emmer | |
| 2004/0078033 A1 | 4/2004 | Levin | |
| 2004/0215178 A1 | 10/2004 | Maurice | |
| 2005/0016185 A1 | 1/2005 | Emmer | |
| 2005/0038422 A1 | 2/2005 | Maurice | |
| 2005/0056027 A1 | 3/2005 | White | |
| 2005/0086949 A1 | 4/2005 | Noble | |
| 2005/0106153 A1 | 5/2005 | Nordouist | |
| 2005/0177147 A1 | 8/2005 | Vancelette | |
| 2005/0192564 A1 | 9/2005 | Cosman | |
| 2005/0214268 A1 | 9/2005 | Cavanagh | |
| 2005/0274142 A1 | 12/2005 | Corey | |
| 2006/0049274 A1 | 3/2006 | Hume | |
| 2006/0053165 A1 | 3/2006 | Hume | |
| 2006/0079867 A1 | 4/2006 | Berzak | |
| 2006/0122590 A1 | 6/2006 | Bliweis | |
| 2006/0155267 A1 | 7/2006 | Berzak | |
| 2006/0155268 A1 | 7/2006 | Amir | |
| 2006/0264920 A1 | 11/2006 | Duong | |
| 2006/0293647 A1 | 12/2006 | McRae | |
| 2007/0000259 A1 | 1/2007 | Brook | |
| 2007/0093710 A1 | 4/2007 | Maschke | |
| 2007/0129626 A1 | 6/2007 | Mahesh | |
| 2007/0129629 A1 | 6/2007 | Beauregard | |
| 2007/0149959 A1 | 6/2007 | DeLonzor | |
| 2007/0166171 A1 | 7/2007 | Kondo | |
| 2007/0167939 A1 | 7/2007 | Duong | |
| 2007/0276360 A1 | 11/2007 | Johnston | |
| 2008/0027419 A1 | 1/2008 | Hamel | |
| 2008/0051774 A1 | 2/2008 | Ofir | |
| 2008/0051776 A1 | 2/2008 | Bliweis | |
| 2008/0115509 A1 | 5/2008 | Gullickson | |
| 2008/0119834 A1 | 5/2008 | Vancelette | |
| 2008/0119838 A1 | 5/2008 | Vancelette | |
| 2008/0319433 A1 | 12/2008 | Geiselhart | |
| 2009/0011032 A1 | 1/2009 | LePivert | |

FOREIGN PATENT DOCUMENTS

| | | |
|---|---|---|
| DE | 202004008875 U1 | 8/2004 |
| DE | 102005050344 | 5/2007 |
| EP | 0292922 B1 | 11/1988 |
| EP | 395307 A2 | 10/1990 |
| EP | 570301 | 11/1993 |
| EP | 955012 | 11/1999 |
| EP | 919197 B1 | 2/2005 |
| GB | 1108905 | 4/1968 |
| GB | 1402737 | 8/1975 |
| GB | 1473856 | 5/1977 |
| GB | 1534472 | 12/1978 |
| GB | 2336781 | 11/1999 |
| GB | 2409815 A1 | 7/2005 |
| JP | 2004041428 A2 | 2/2004 |
| JP | 2007144180 A2 | 6/2007 |
| JP | 2007167100 | 7/2007 |
| WO | WO8303961 A1 | 11/1983 |
| WO | WO9637158 A1 | 11/1996 |
| WO | WO9639960 A1 | 12/1996 |
| WO | WO9947876 A1 | 9/1999 |
| WO | WO0137919 A2 | 5/2001 |
| WO | WO0141683 A2 | 6/2001 |
| WO | WO0197702 | 12/2001 |
| WO | WO0202026 A1 | 1/2002 |
| WO | WO03015651 A1 | 2/2003 |
| WO | WO2004051409 A2 | 8/2004 |
| WO | WO2004089183 A1 | 10/2004 |
| WO | WO2004060465 | 2/2005 |
| WO | WO2004093635 A2 | 6/2005 |
| WO | WO2005098308 A1 | 10/2005 |
| WO | WO2005000106 A2 | 12/2005 |
| WO | WO2006116457 A2 | 11/2006 |
| WO | WO2006127467 | 11/2006 |
| WO | WO2007028232 A1 | 3/2007 |
| WO | WO2007086056 A2 | 8/2007 |
| WO | WO2007129308 | 11/2007 |

OTHER PUBLICATIONS

International Search Report and Written Opinion dated Nov. 5, 2008 in corresponding International Application No. PCT/IL2008/000794.

Qi et al., Development and performance test of a cryoprobe with heat transfer configuration enhancement, Cryogenics, 2006, pp. 881-887, vol. 46, Elsevier.

International Search Report dated Mar. 25, 2010 in corresponding International Application No. PCT/IB2009/052615.

International Search Report and Written Opinion dated Jul. 23, 2009 in corresponding International Application No. PCT/IL2009/000062.

International Search Report and Written Opinion dated Dec. 22, 2008 in corresponding International Application No. PCT/IL2008/001114.

International Search Report and Written Opinion dated Sep. 4, 2009 in corresponding International Application No. PCT/IB2009/051532.

Office Action dated Jan. 22, 2010 in Application No. EP 07805563.9.

International Search Report and Written Opinion dated Nov. 28, 2008 in corresponding International Application No. PCT/IL2008/000943.

International Search Report and Written Opinion dated Jan. 29, 2008 in corresponding International Application No. PCT/IL2007/001103.

International Search Report and Written Opinion dated Jan. 30, 2008 in corresponding International Application No. PCT/IL2007/001142.

International Search Report and Written Opinion dated Nov. 6, 2007 in corresponding International Application No. PCT/IL2007/000974.

Qi et al., Flow boiling of liquid nitrogen in micro-tubes: Part I—onset of nucleate boiling, two phase flow instability and two phase flow drop, International Journal of Heat and Mass Transfer, 2007, pp. 4999-5016, vol. 50, Elsevier.

Qi et al., Flow boiling of liquid nitrogen in micro-tubes: Part II—heat transfer characteristics and critical heat flux, International Journal of Heat and Mass Transfer, 2007, pp. 5017-5030, vol. 50, Elsevier.

Zhang et al., Two phase flow characteristics of liquid nitrogen in vertically upward 0.5 and 1.0 mm micro-tubes: Visualization studies, Cryogenics, 2009, pp. 565-575, vol. 49, Elsevier.

International Search Report and Written Opinion dated Aug. 24, 2010 in corresponding International Application PCT/US2010/34467.

U.S. Appl. No. 12/360,221, filed Jan. 27, 2009, Levin, Arbel Medical Ltd.

U.S. Appl. No. 11/851,055, filed Sep. 6, 2007, Toubia et al., Arbel Medical Ltd.

U.S. Appl. No. 12/017,035, filed Jan. 20, 2008, Toubia et al., Arbel Medical Ltd.

U.S. Appl. No. 11/763,093, filed Jun. 14, 2007, Levin et al., Arbel Medical Ltd.

U.S. Appl. No. 12/278,733, filed Nov. 5, 2008, Levin et al., Arbel Medical Ltd.

U.S. Appl. No. 11/857,085, filed Sep. 18, 2007, Levin et al., Arbel Medical Ltd.

U.S. Appl. No. 12/668,428, filed Sep. 7, 2010, Levin et al.

U.S. Appl. No. 12/673,506, filed Feb. 15, 2010, Levin et al.

U.S. Appl. No. 12/237,805, filed Sep. 25, 2008, Levin et al., Arbel Medical Ltd.

U.S. Appl. No. 12/313,611, filed Nov. 21, 2008, Toubia et al., Arbel Medical Ltd.

U.S. Appl. No. 12/812,819, filed Sep. 29, 2010, Toubia et al., IceCure Medical Ltd.

U.S. Appl. No. 12/988,233, filed Oct. 15, 2010, Toubia et al., Arbel Medical Ltd.

U.S. Appl. No. 12/611,938, filed Nov. 4, 2009, Levin.

U.S. Appl. No. 12/700,761, filed Feb. 5, 2010, Levin.

U.S. Appl. No. 12/778,172, filed May 12, 2010, Berzak et al., IceCure Medical Ltd.

U.S. Appl. No. 12/846,047, filed Jul. 29, 2010, Berzak et al., IceCure Medical Ltd.

* cited by examiner

CRYOSURGICAL INSTRUMENT WITH ENHANCED HEAT TRANSFER

BACKGROUND

1. Technical Field

Embodiments of the present invention relate generally to cryosurgical equipment, and, more particularly, to cryosurgical treatment methods and devices with enhanced heat transfer between an external surface and internal fluid cryogen.

2. Description of Related Art

Cryoprobes that "boil" a liquid cryogen, when this liquid cryogen is supplied from an external source into the cryoprobe, are known for performing cryosurgical procedures. Generally, a cryogen is delivered into a cryoprobe in the form of two-phase fluid. This is caused by the fact that a certain fraction of the liquid cryogen is evaporated inevitably on the way to the cryoprobe as a result of imperfect thermal insulation of the delivery hose. The cryogen two-phase condition cannot be improved by separating between the liquid and gaseous phases completely in the internal cavity of the cryotip (the distal section of the cryoprobe) without application of special measures. In addition, in particular for the use of nitrogen as a cryogen, the liquid nitrogen interact with solid warmer surface by creating nitrogen gas cushion, known as Liedenfrost effect, thus reduce considerably the ability to absorb heat from the warmer surface. Without such special means, it is impossible to completely use the liquid fraction of the cryogen for effective freezing of a treated tissue, forcing the partial change of phase of the fluid cryogen to take place as close as possible to the targeted surface.

Solutions to this problem are known. For example, U.S. Pat. No. 4,726,194 features a conduit with active heating thereof through which liquid nitrogen flows. The conduit terminates in an expansion chamber that is filled with cotton wool, in order to expand the volume available for boiling.

Another example is U.S. Pat. No. 4,082,096, which features a deformable mass that receives liquid cryogen, surrounded by a membrane that is impervious to liquid nitrogen.

Other examples include U.S. Pat. Nos. 5,520,682, 6,565, 556, 4,946,460, 7,189,228 and 5,674,218, each of which features an expansion chamber.

BRIEF SUMMARY

The background art does not provide a solution that overcomes the problem of causing the boiling to take place close to the warmer surface within a cryosurgical instrument such as a cryoprobe.

The Applicants have discovered an advantageous solution to the problems of the background art by considering the nature of boiling nitrogen fluid flow. Their discovery provides solutions that are not encumbered by the drawbacks of the background art.

Embodiments of the present invention provide a cryosurgical instrument with a uniquely positioned and arranged heat exchanger. The heat exchanger is in a cryogen supply passage and/or in a cryotip. Such a construction/arrangement facilitates heat exchange with a cryogen.

Embodiments of the present invention overcome the above problems of the background art by forcing the fluid to flow through a annular cooling passage, by forcing the fluid under pressure onto the inner surface of the cryosurgical instrument, or by cooling an enhancing element of which at least a portion is in direct contact with the outer surface of the cryosurgical instrument, or a combination thereof.

The reduced cross section for the flow close to the inner surface of the cryosurgical instrument, and the expansion of the fluid through partial change of phase process, increases the speed of the flow considerably, and thus increases heat transfer from the inner surface to the fluid. The structure permits the two-phase cryogen flow both into and out of the cryosurgical instrument while controlling temperature transfer at the desired specific locations or elements within that structure. In case of forcing the fluid onto the inner surface of the instrument, the boiling occurs closer to the surface, thus increasing the heat transfer. Bringing the liquid phase of the fluid near the internal surface of the cryotip and directing the obtained liquid phase on the internal surface with following its boiling and evaporation in order to solve the above problem. The element can be made of either metal or ceramic or any other materials that maintain its integrity under the low temperature of the boiling conditions of the cryogenic fluid.

One aspect of the present invention provides a cryosurgical instrument that includes: a tubular housing having a longitudinal axis, a proximal end, and a tip at distal end; a cryogen supply passage extending from the proximal end to the distal end along the longitudinal axis, the cryogen supply passage having an upstream portion proximate to the proximal end and a downstream portion proximate to the distal end; a heat exchange enhancing member in the housing, disposed along the longitudinal axis, and surrounding at least some of the downstream portion of the supply passage; an annular cooling passage between the heat exchange enhancing member and the tubular housing, the annular cooling passage in communication with a cryogen exhaust passage, cryogen in the annular cooling passage absorbing heat in the annular cooling passage; a tip cooling and cryogen flow directing section at the distal end and in communication with the cryogen supply passage, the tip cooling and cryogen flow directing section deflecting a flow of cryogen flow to the tip so as to cool the tip, and an insulation element in the tubular housing, disposed along the longitudinal axis, surrounding a portion of the cryogen supply passage, and between the proximal end and the heat exchange enhancing member, the insulation element and the downstream end of the cryogen supply passage defining bounds of a heat exchanging zone.

Another aspect of the present invention provides a cryosurgical instrument that includes: a tubular housing having a longitudinal axis, a proximal end, and a tip distal end; a cryogen supply passage extending from the proximal end to the distal end along the longitudinal axis, the supply passage having an upstream portion proximate to the proximal end and a downstream portion proximate to the distal end; a heat exchange enhancing member in the housing, disposed along the longitudinal axis, and surrounding at least some of the downstream portion of the supply passage, the enhancing member having a plurality of return channels circumferentially disposed about the longitudinal axis and extending longitudinally through the enhancing member; a flow deflector between the tip and the supply passage, the flow director adapted and configured to deflect a cryogen flow exiting from the supply passage to the return channels and to absorb heat, thereby cooling the tip, the flow director fixedly and spacedly disposed from the supply passage. The flow of cryogen in the cryogen supply passage urges cryogen that has exited the cryogen supply passage to flow into the return channels. The sum of cross-sectional areas of the plurality of return channels is about equal to a cross-sectional area of the supply passage.

Another aspect of the present invention provides a cryoprobe that includes: a tubular housing having a longitudinal axis, a proximal end and a tip at a distal end; a heat exchange enhancing member in the housing, disposed along the longitudinal axis, proximate to the distal end, the enhancing member having a cryogen supply passage extending therethrough along the longitudinal axis and having an radial flow section through which cryogen flows radially through the enhancing member; an peripheral return passage between the enhancing member and the tubular housing, the peripheral return passage in communication with the radial flow section and a cryogen exhaust passage; and a tip cooling and cryogen flow directing section at the distal end and in communication with the cryogen supply passage, the tip cooling and cryogen flow directing section transmitting a temperature of a cryogen flow to the tip. The flow of cryogen in the cryogen supply passage urges cryogen through the radial flow section into the peripheral return passage.

Still another aspect of the present invention provides a cryosurgical instrument that includes: a shaft having a central axis, an upstream cryogen supply section, a downstream heat exchanging zone, and a solid tip at an end of the shaft opposite the cryogen supply section; a heat exchange enhancing member in the heat exchanging zone in the shaft and extending along the central axis, the enhancing member having a axial cryogen delivery passage extending therethough along the central axis; a cryogen return passage between the heat exchange enhancing member and the shaft; and a cryogen flow deflector between the tip and the heat exchange enhancing member, the deflector spaced from the enhancing member and adapted and configured to deflect expanded cryogen into the return passage. The cryosurgical instrument does not include a cryogen expansion chamber.

Yet another aspect of the presents a cryosurgical instrument that includes: a shaft having a central axis, an upstream cryogen supply section, a downstream heat exchanging zone, and a solid tip at an end of the shaft opposite the cryogen supply section; a heat exchange enhancing member in the heat exchanging zone in the shaft and extending along the central axis, the enhancing member having an axial cryogen delivery passage extending therethough along the central axis and a cryogen return passage; and a cryogen flow deflector between the tip and the heat exchange enhancing member, the deflector spaced from the enhancing member and adapted and configured to deflect cryogen into the return passage. The cryosurgical instrument does not include a cryogen expansion chamber.

A further aspect of the present invention provides a method of treatment with a cryosurgical instrument. The method includes: providing a cryosurgical instrument; inserting the cryosurgical instrument into tissue to be treated; delivering cryogen to a supply passage of the cryosurgical instrument; reflecting cryogen from the supply passage, via a reflecting surface that closes off a tip of the cryosurgical device; and forcing cryogen through a heat exchange zone of the cryosurgical instrument, such that partial change of phase occurs at the reflecting surface and at the heat exchange zone.

Still another aspect of the present invention provides a method of treatment with a cryosurgical instrument. The method comprises: providing a cryosurgical instrument; inserting the cryosurgical instrument into tissue to be treated; delivering cryogen via a supply passage of the cryosurgical instrument to a hollow tip of the cryosurgical instrument so that the cryogen boils at the tip; and reflecting cryogen from the supply passage, via a reflecting surface that closes off a tip of the cryosurgical device.

These, additional, and/or other aspects and/or advantages of the present invention are: set forth in the detailed description which follows; possibly inferable from the detailed description; and/or learnable by practice of the present invention.

BRIEF DESCRIPTION OF THE DRAWINGS

The present invention will be more readily understood from the detailed description of embodiments thereof made in conjunction with the accompanying drawings of which:

FIG. 1c is a cross-sectional view of the cryoprobe of FIG. 1a along line I of FIG. 1a;

FIG. 3b is a cross-sectional view of the cryoprobe of FIG. 3a taken along line II of FIG. 3a;

FIG. 4b is a cross-sectional view of the cryoprobe of FIG. 4a along line III of FIG. 4a;

FIG. 5b is a cross-sectional view of the cryoprobe of FIG. 5a along line IV of FIG. 5a;

FIG. 6b is a cross-sectional view of the cryoprobe of FIG. 6a along line V of FIG. 6a.

DETAILED DESCRIPTION

Figure 1A:
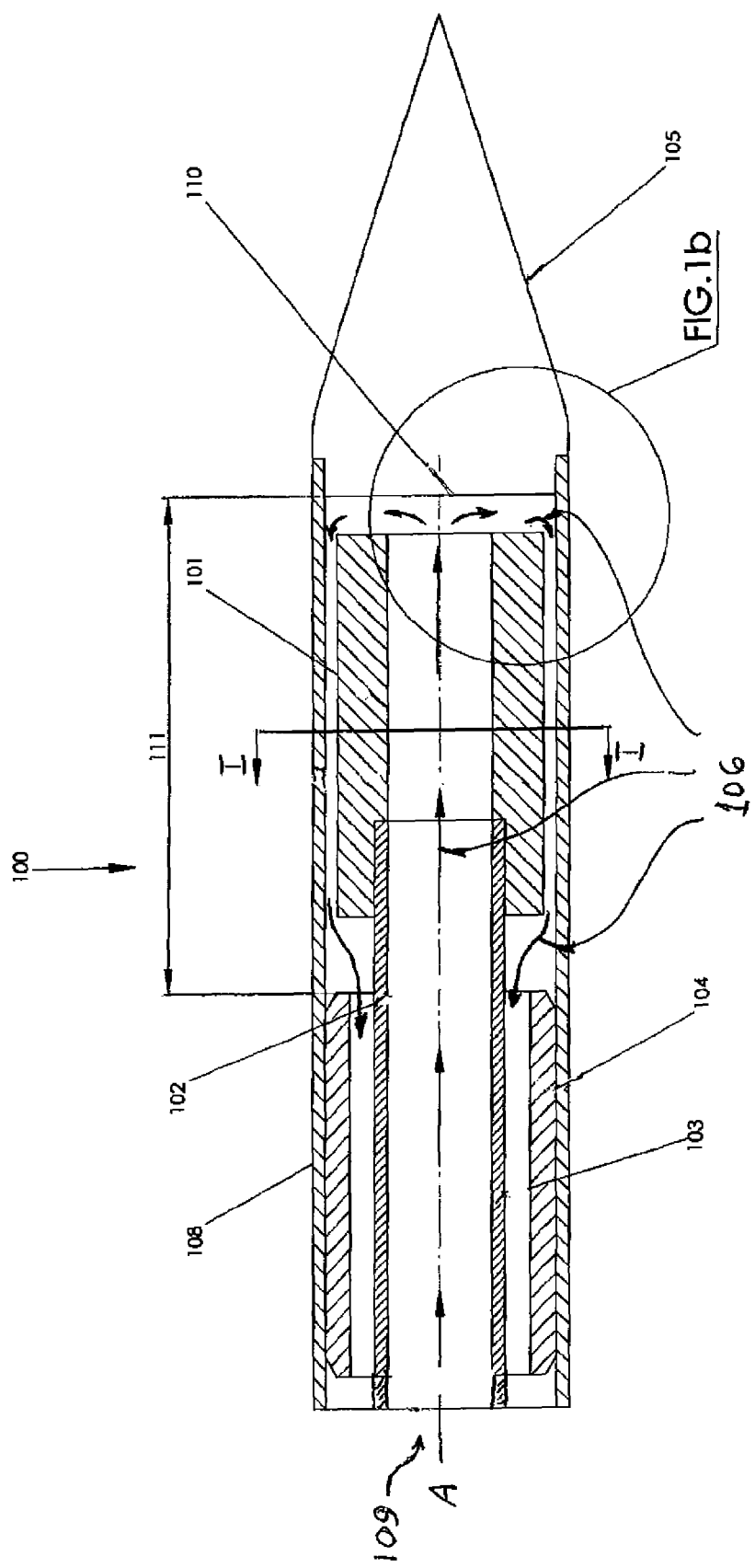
FIG. 1a is a longitudinal cross-sectional view of a cryoprobe consistent with an embodiment of the present invention, with an annular cooling passage provided for return flow and a closed tip.

Reference will now be made in detail to embodiments of the present invention, examples of which are illustrated in the accompanying drawings, wherein like reference numerals refer to the like elements throughout. The embodiments are described below to explain the present invention by referring to the figures.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

The term "cryosurgical instrument" refers herein to any type of cryo instrument, including but not limited to cryoprobes and cryocatheters. Although the description centers around cryoprobes, this is for the purpose of illustration only and is without any intention of being limiting.

Figure 1B:
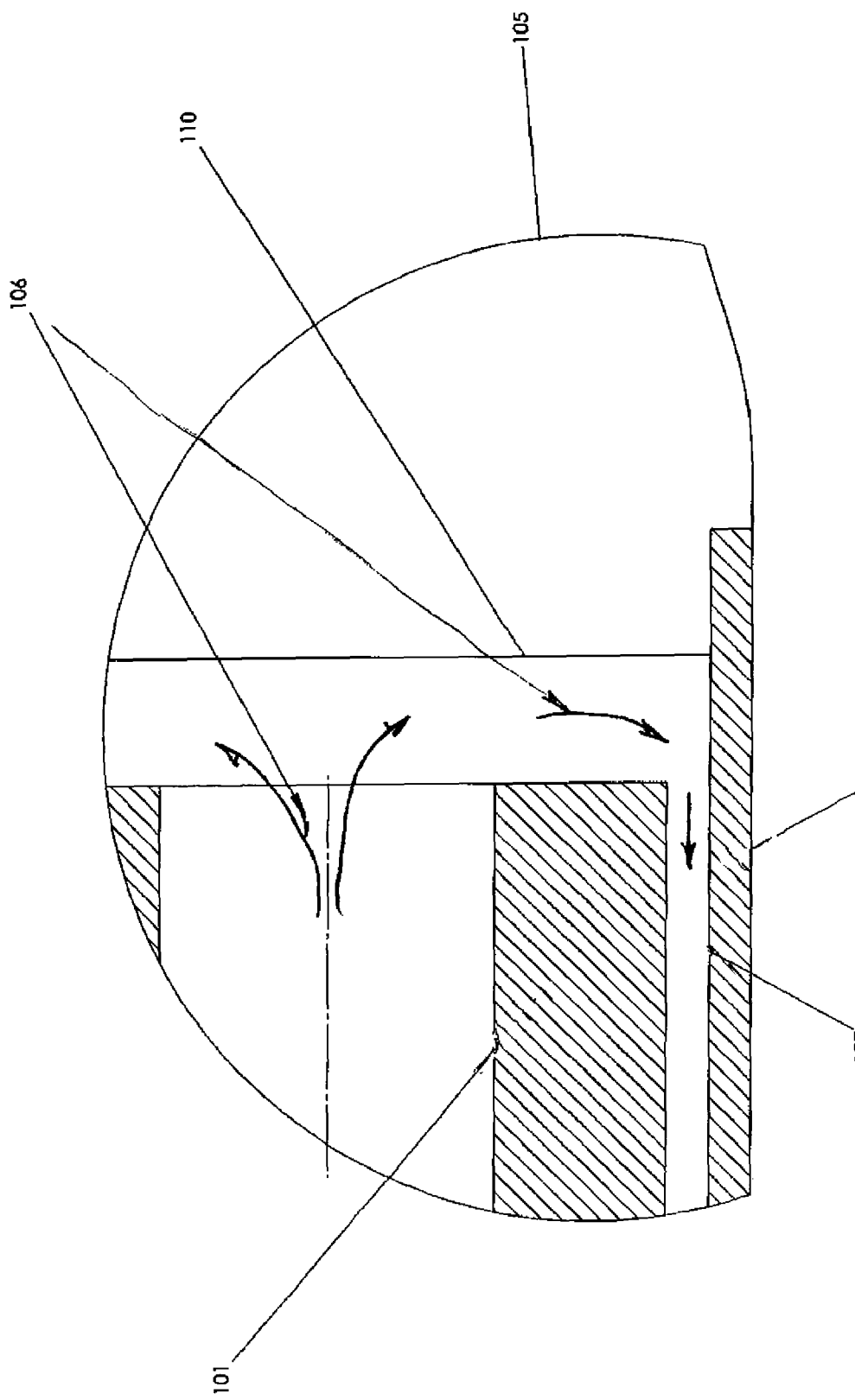
FIG. 1b shows a portion of the cryoprobe of FIG. 1a in more detail.
Figure 1C:
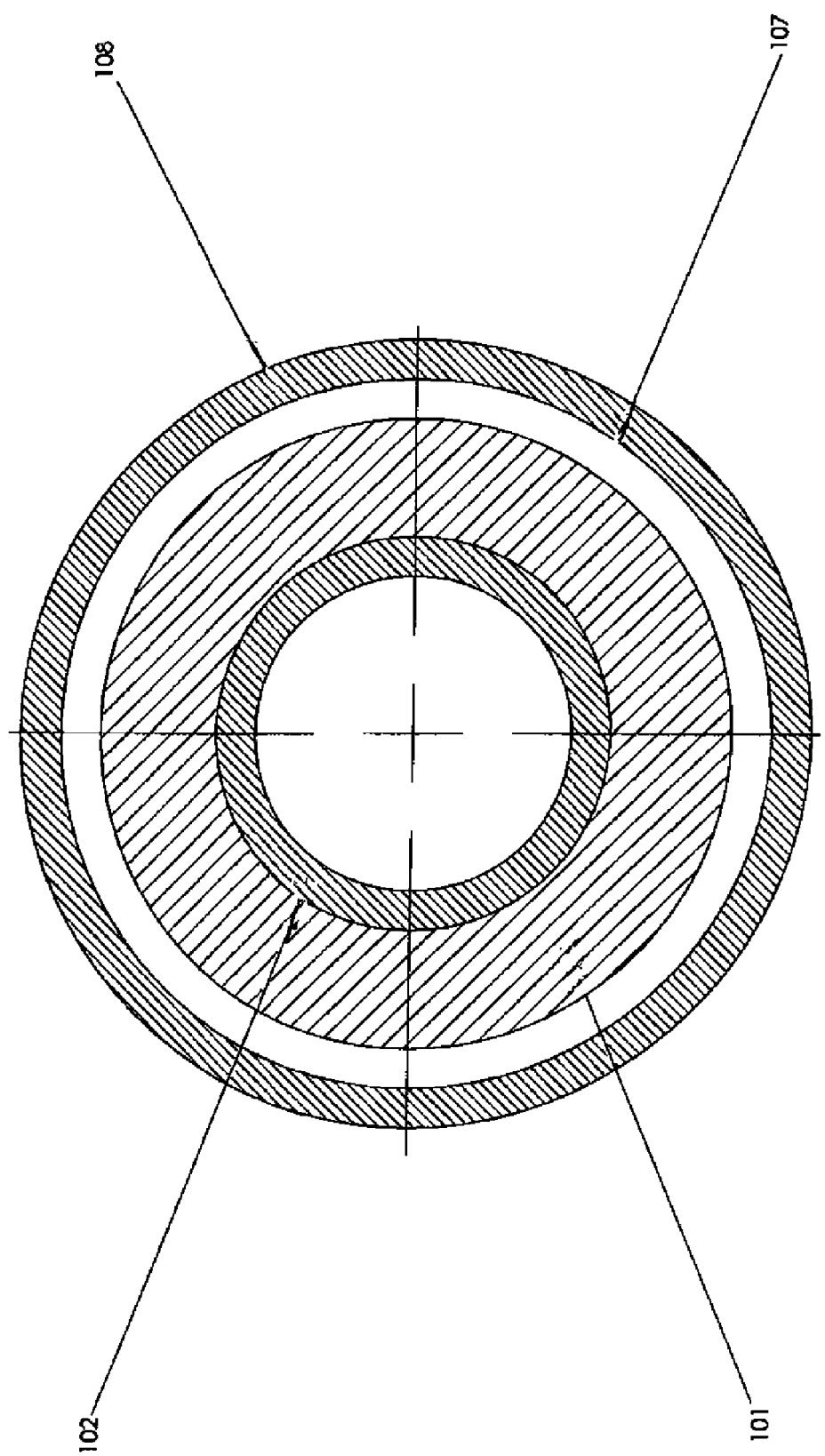

Referring to FIGS. 1a-1c, cryoprobe 100 comprises a tubular housing 108, having a longitudinal axis, a proximal end and a tip 105 (cryotip) at the distal end. Preferably tip 105 is a closed, optionally solid, tip, closed at its proximal end by a reflecting surface 110, which acts as a cryogen direction section, to reverse the flow of cryogen. Reflecting surface 110 also transmits the temperature of the cryogen flow to tip 105, and also separates tip 105 from a cryogen supply passage 102. Cryogen supply passage 102 extends from the proximal end to the distal end along the longitudinal axis, cryogen supply passage 102 has an upstream portion proximate to the proximal end and a downstream portion proximate to the distal end. Cryogen supply passage 102 receives cryogen from a cryogen inlet 109 and supplies the cryogen to the reflecting surface 110. Reflecting surface 110 is shown as flat perpendicular surface with respect to the flow direction, however other shapes and orientations of reflecting surfaces can be employed to change the direction of the incoming flow towards the return cooling passage. Optionally and preferably as shown, cryoprobe 100 lacks an expansion chamber.

The return cryogen enters an annular cooling passage 107 between the heat exchange enhancing element 101 and the inner surface of the tubular housing 104, increasing the velocity of the cryogen and enhancing heat transfer between the cryoprobe 100 and the cryogen. The heat exchange zone 111 is indicated with arrows; heat is absorbed from the external environment at heat exchange zone 111. The cryogen then leaves the cryoprobe through a cryogen exhaust passage 103.

Thermal insulation 104 preferably terminates the heat transfer from the cryoprobe 100 and the cryogen flow in the cryogen exhaust passage 103, thereby determining the boundaries of the heat exchange zone 111.

FIG. 1b shows heat exchange enhancing element 101, tip 105, annular cooling passage 107 and tubular housing 108 in more detail. In addition, the direction of cryogen flow is shown with arrows 106, as the cryogen reaches reflecting surface 110, and then returns through annular cooling passage 107. The dimensions of annular cooling passage 107 are preferably adjusted so as to provide the above described increased cryogen velocity, such that preferably a cross-sectional area of the annular cooling passage 107 is of the same order as the cross-sectional area of the supply passage 102 and wherein a velocity of a flow of cryogen in the return passage 107 is greater than a velocity of a flow of cryogen in the supply passage 102; for a typical cryoprobe, such dimensions of the annular cooling passage 107 would optionally and preferably be up to 1-2 mm but more preferably are 0.1 mm to 0.3 mm. Also reflecting surface 110 is preferably constructed of any suitable material for transmitting cold to tip 105, which is itself constructed of a suitable material for becoming cold; non-limiting illustrative examples of materials for both components include but are not limited to metals, whether pure, alloys or composites, that are thermally conductive.

In the operation of cryoprobe 100, cryogen enters through cryogen inlet 109 to cryogen supply passage 102, and travels down cryogen supply passage 102 until it reaches reflecting surface 110. The cryogen then cools tip 105 and then returns through annular cooling passage 107 and is exhausted through annular exhaust passage 103.

Figure 2:
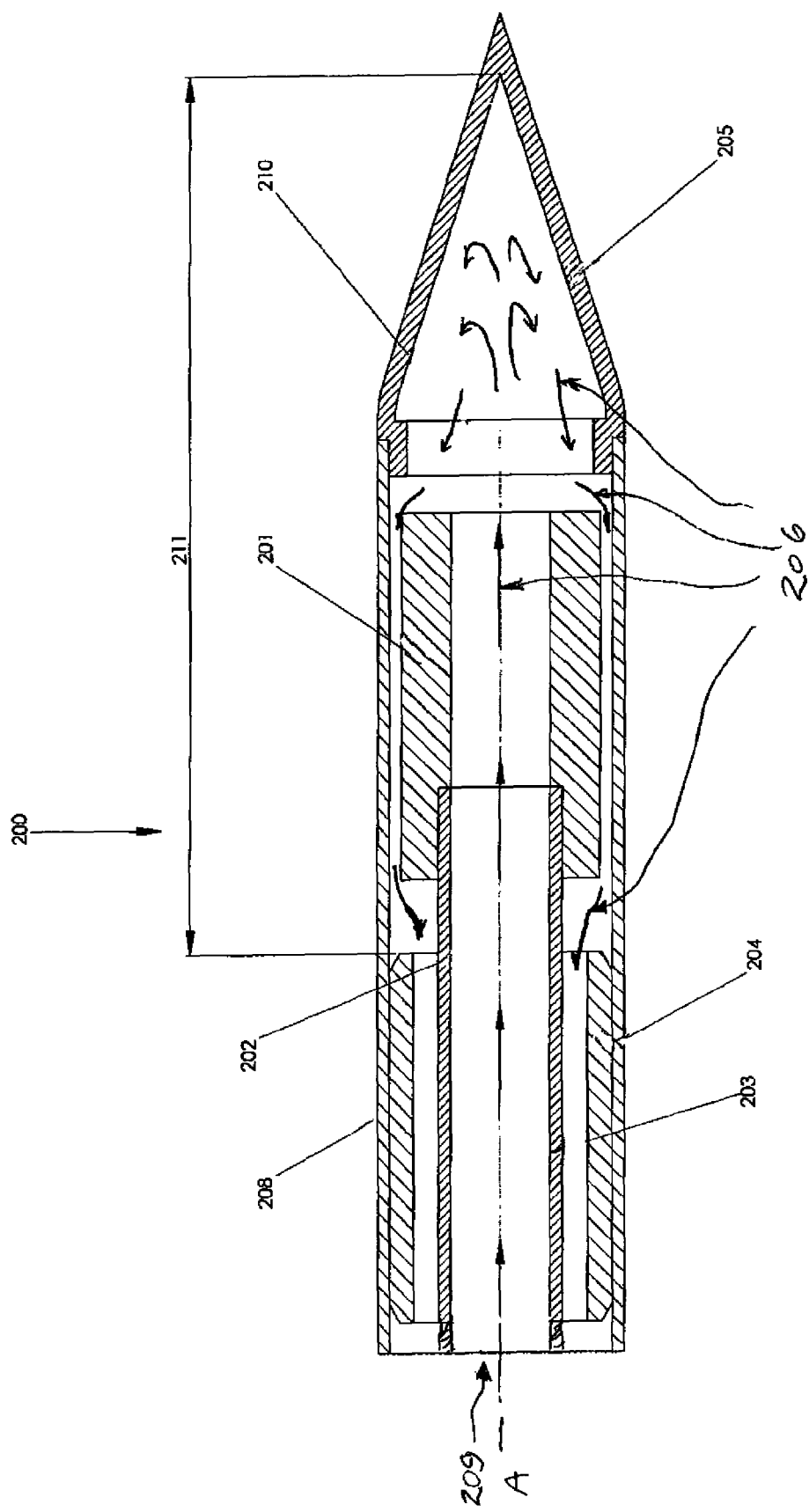
FIG. 2 is a longitudinal cross-sectional view of a cryoprobe consistent with an embodiment of the present invention, with an annular cooling passage provided for return flow for an open cryotip.

Referring to FIG. 2, cryoprobe 200 is similar in construction to cryoprobe 100, except that cryoprobe 200 features a hollow tip 205. An expansion chamber 210 is located within tip 105 (in place of the above described reflecting surface of cryoprobe 100 of FIGS. 1a and 1b).

In the operation of cryoprobe 200, cryogen enters through cryogen inlet 209 to cryogen supply passage 202, and travels down cryogen supply passage 202 until it enters expansion chamber 210. The cryogen then expands and cools tip 205 directly within expansion chamber 210. The partially phase changed cryogen then returns through annular cooling passage 207 and is exhausted through cryogen exhaust passage 203.

The expansion chamber 210 is in communication with the downstream portion of the supply passage 202 and arranged (i) to permit cryogen exiting from the supply passage 202 to expand and to cool the tip 205, and (ii) to direct expanded cryogen that has exited the cryogen supply passage 202 to flow into the annular cooling passage 207. Due to heat absorption from the surrounding in contact with 205, the heat exchanging zone 211 increases to include the tip 205.

Figure 3A:
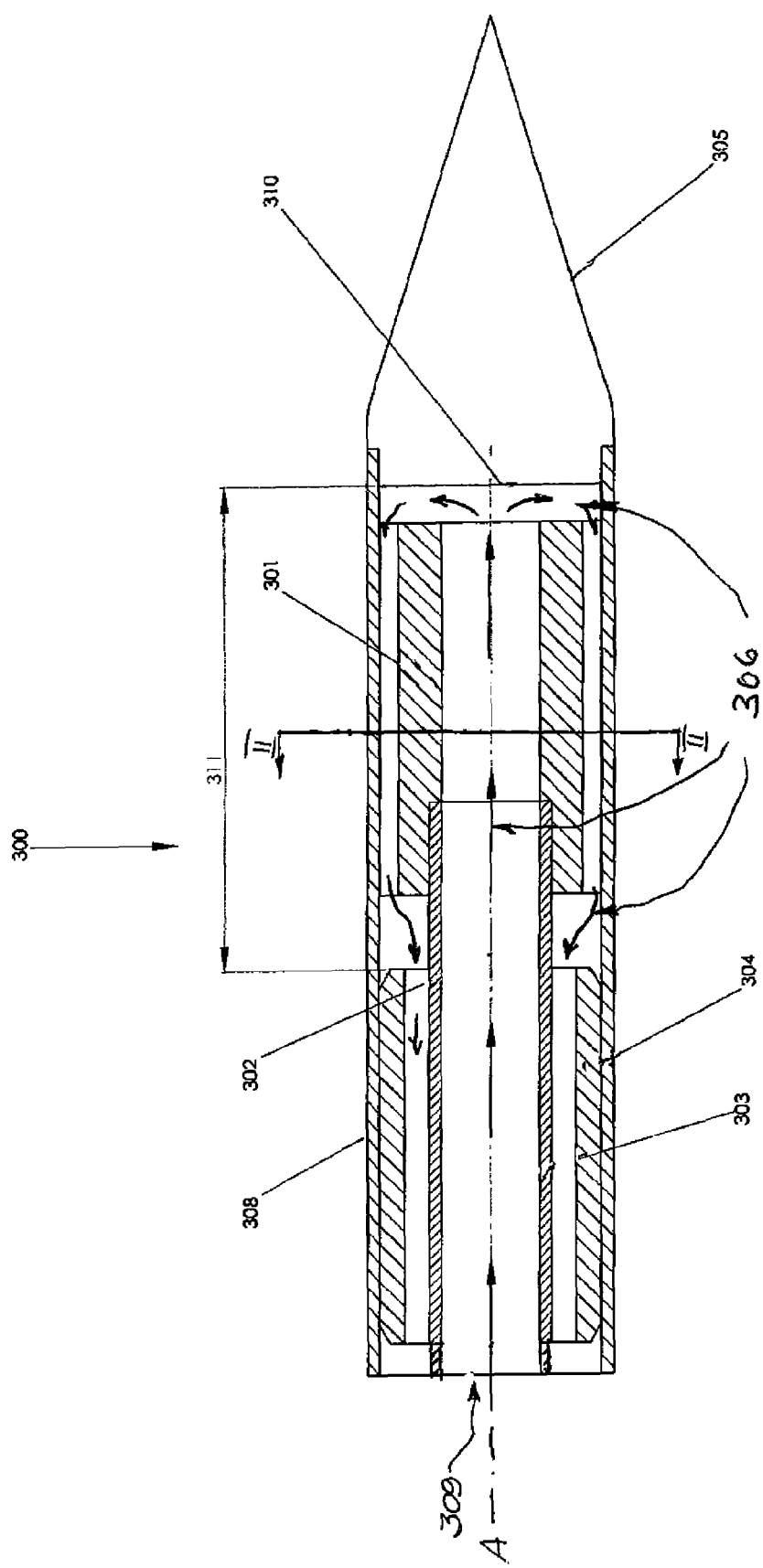
FIG. 3a is a longitudinal cross-sectional view of a cryoprobe consistent with an embodiment of the present invention, with a plurality of grooves provided for return cryogen flow for a closed cryotip and for improved temperature transfer.
Figure 3B:
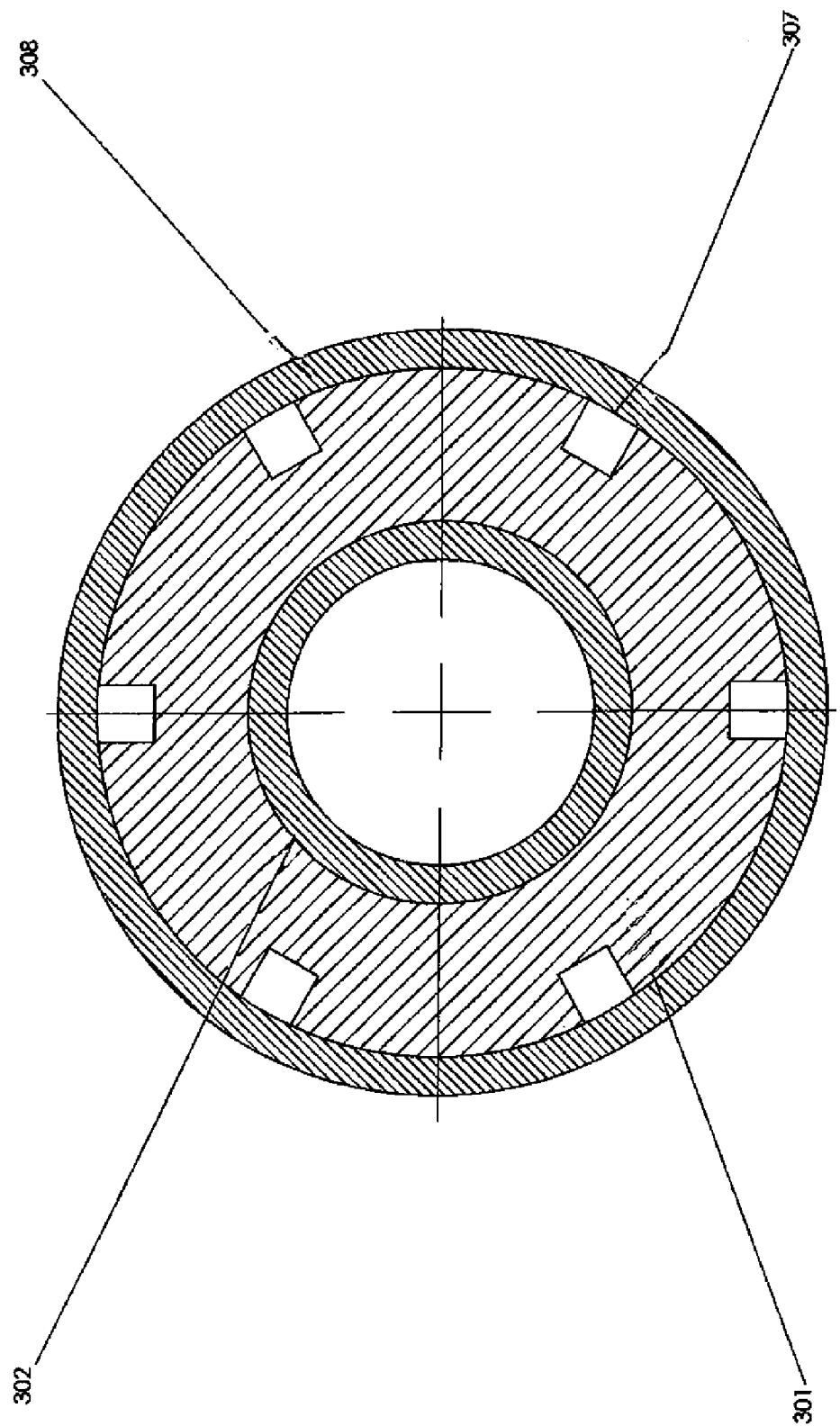

Referring to FIGS. 3 and 3b, cryoprobe 300 features a closed, optionally solid, tip 305 and a reflecting surface 310 preferably located at tip 305. Like cryoprobe 100, cryoprobe 300 preferably lacks an expansion chamber, as shown. Unlike cryoprobe 100, cryoprobe 300 features a plurality of grooves 307, which are preferably straight grooves and which function as a plurality of return channels for receiving the expanded return cryogen; grooves 307 are preferably in communication with a cryogen exhaust passage 303 for then exhausting the cryogen out of cryoprobe 300. Grooves 307 surround at least a portion of the downstream portion of the supply passage 302 and are preferably circumferentially disposed about the longitudinal axis and extending longitudinally.

The above construction increases the speed of the return flow. By increasing the speed of the return flow and causing a partial change of phase of the cryogen to take place in the grooves 307, the heat is absorbed from the cryoprobe 300 directly through the boiling at the grooves 307, and indirectly by conducting the heat through the contact surface of 301 with 308. Thermal insulation 304 terminates the heat transfer from the cryoprobe 300. The heat exchange zone 311 is indicated with arrows; heat is absorbed from the external environment at heat exchange zone 311.

As shown in FIG. 3b, cryogen travels through cryogen supply passage 302 and returns through straight grooves 307, which are located at the edge of tubular housing 308.

In the operation of cryoprobe 300, cryogen enters through cryogen inlet 309 to cryogen supply passage 302, and travels down cryogen supply passage 302 until it reaches reflecting surface 310. The cryogen then cools tip 305 by cooling reflecting surface 310 and also by cooling grooves 307. The expanded cryogen then returns through grooves 307 and is exhausted through cryogen exhaust passage 303.

Preferably a sum of cross-sectional areas of the plurality of grooves 307 is about equal to a cross-sectional area of the supply passage 302, and a velocity of a flow of cryogen in the grooves 307 is greater than a velocity of a flow of cryogen in the supply passage 302, due to the partial change of phase.

Figure 4A:
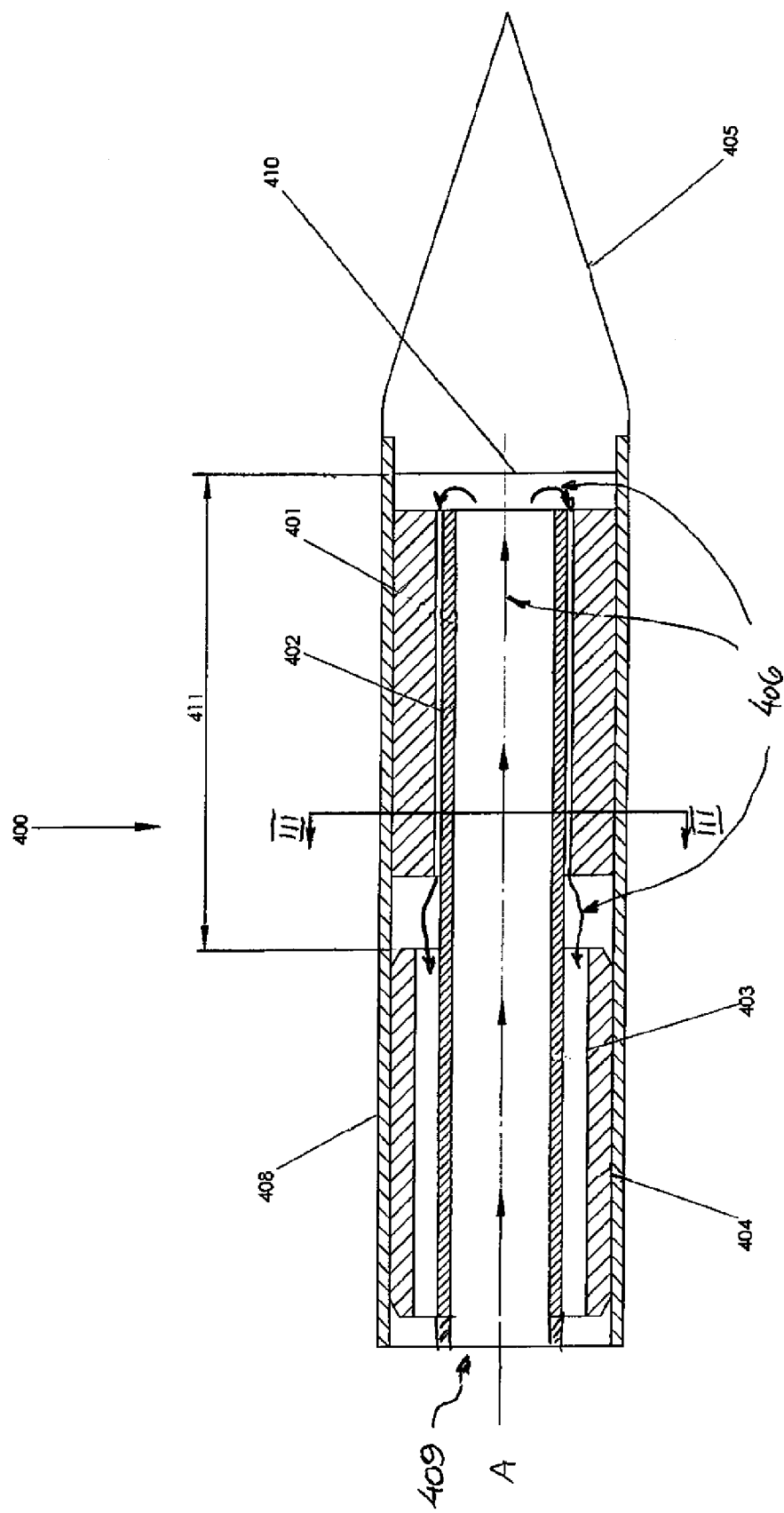
FIG. 4a is a longitudinal cross-sectional view of a cryoprobe consistent with an embodiment of the present invention, with a plurality of grooves provided for return cryogen flow for a closed cryotip.
Figure 4B:
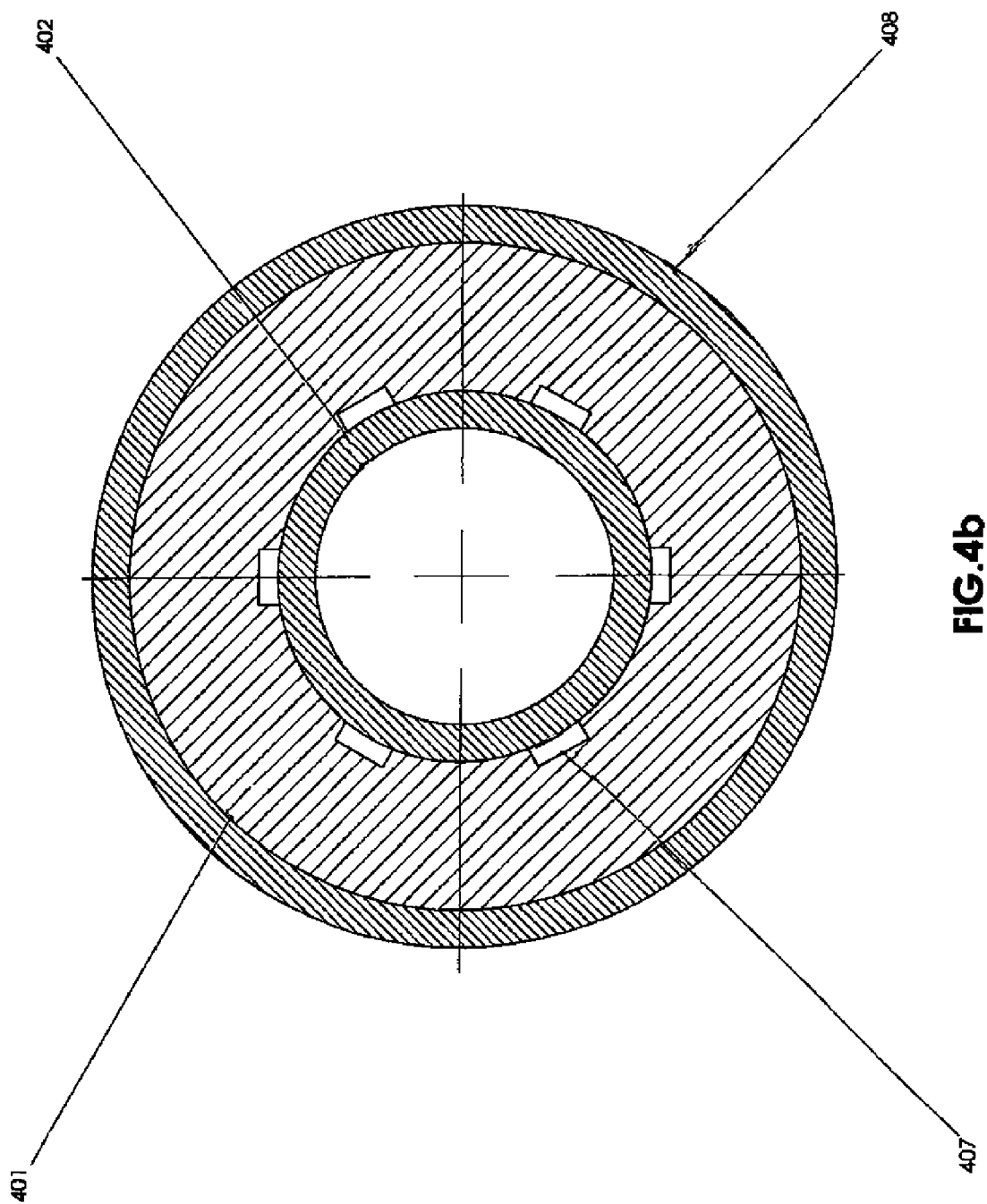

Referring to FIGS. 4a-4c, cryoprobe 400 is similar in construction to cryoprobe 300, except that straight grooves 407 are located internally, close to but external to cryogen supply passage 402, and are sealingly capped by an inner surface of tubular housing 408. The heat exchange zone 411 is indicated with arrows; heat is absorbed from the external environment at heat exchange zone 411. Cryogen absorbs heat from heat exchange enhancing element 401, which in turn absorbs heat from tubular housing 408 in the heat exchange zone 411 through thermal conductivity. Only cools 401 through cryogen supply passage 402 and straight grooves 407.

In both cryoprobes 300 and 400, a two-phase flow of cryogen (liquid and gas) preferably enters to the tip 305 or 405. The two-phase flow is then exposed to the heat absorption surface portion of the tip 305 or 405, and again is exhausted as a two-phase flow. The ratio of gas to liquid is higher in the exhausted two phase flow, however, the opening cross section is similar in size to the cross section of the cryogen exhaust passage 303 or 403, such that the speed of the exhausted two-phase flow is greater.

Figure 5A:
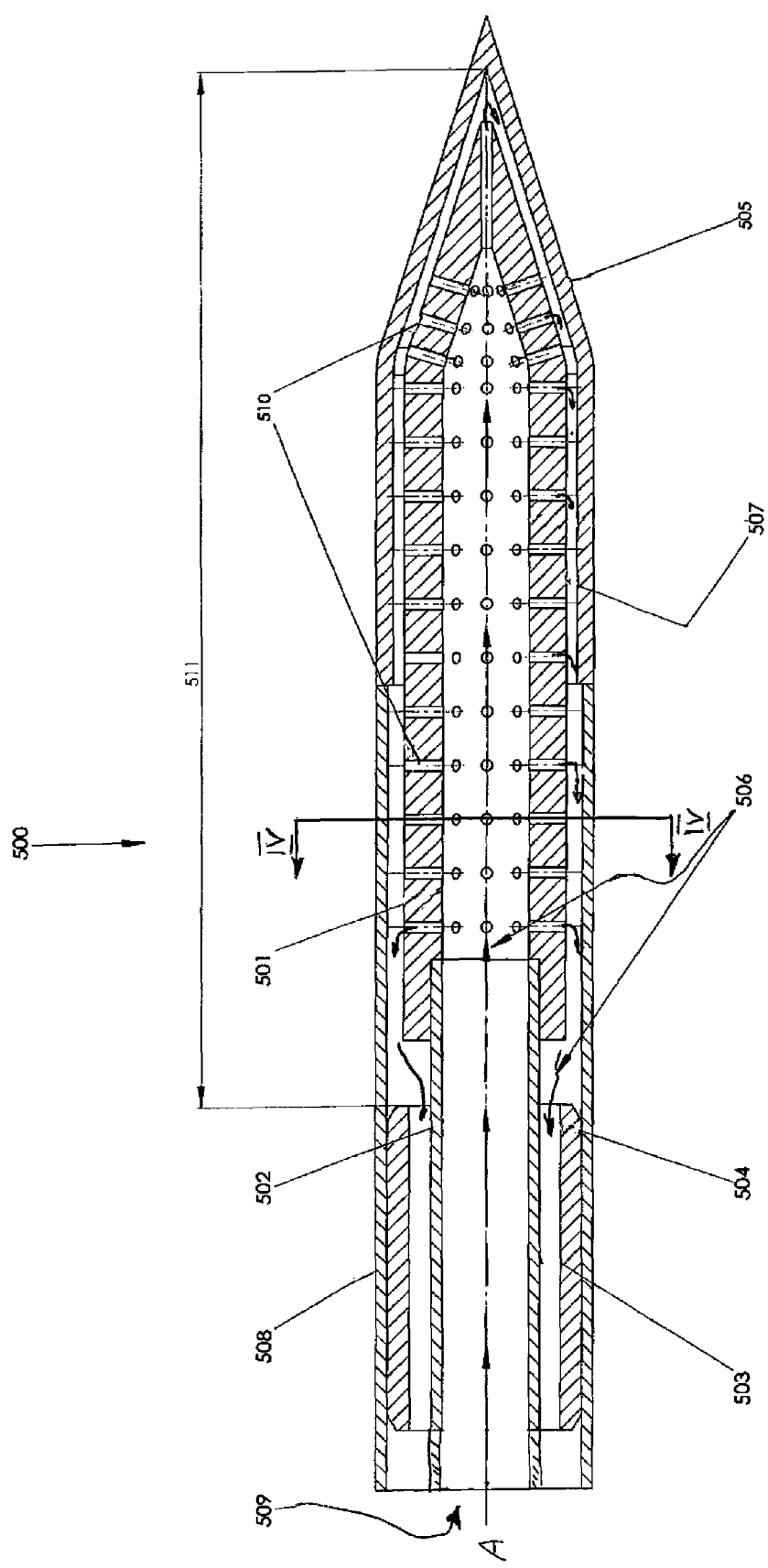
FIG. 5a is a longitudinal cross-sectional view of a cryoprobe consistent with an embodiment of the present invention, with an annular cooling passage provided for return flow for an open cryotip.
Figure 5B:
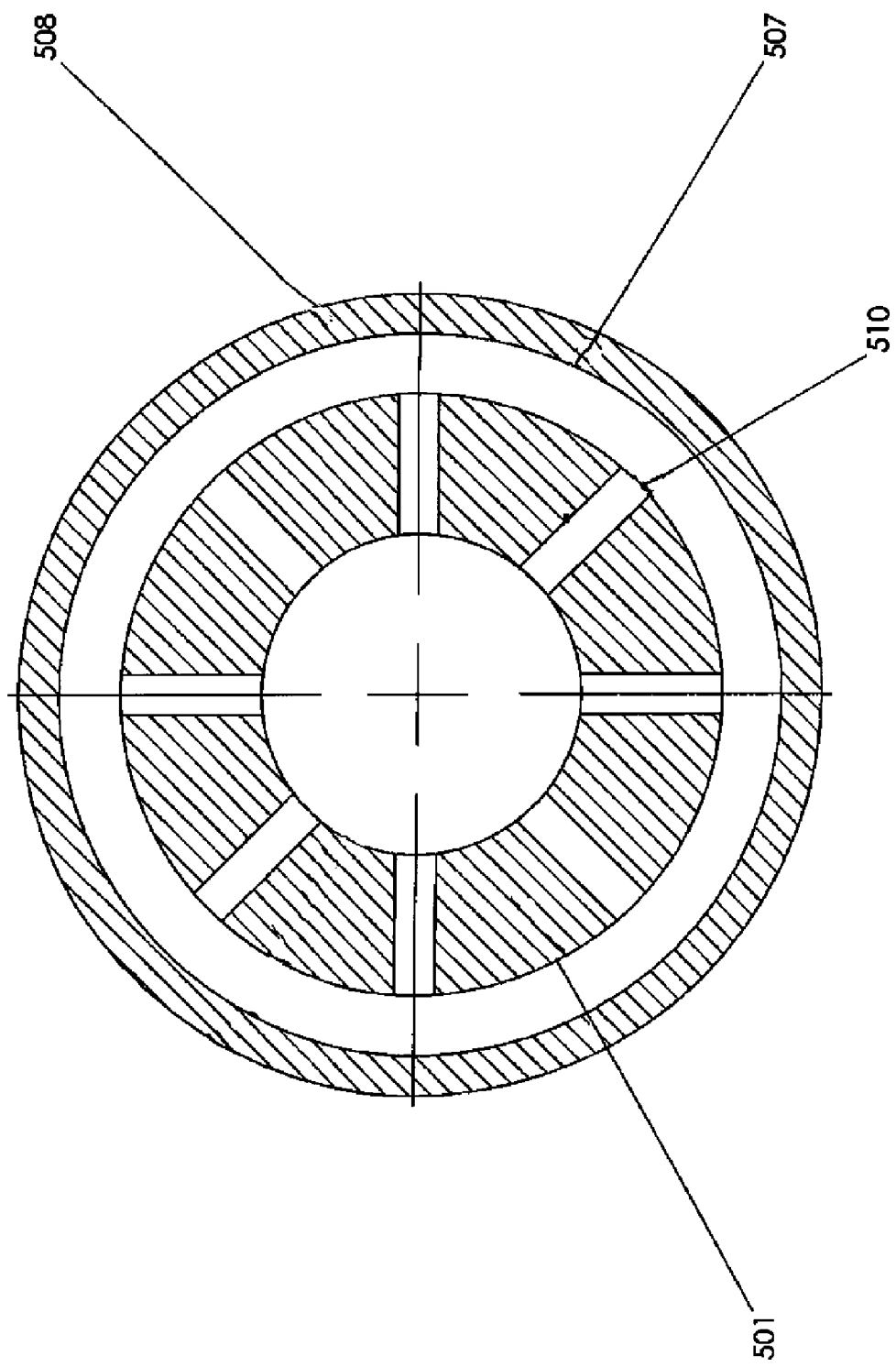

Referring to FIGS. 5a and 5b, cryoprobe 500 features a hollow tip 505 that receives cryogen, and hence cooling, directly from a cryogen supply passage 502. The cryogen returns through a plurality of radial through holes 510 to an annular cooling passage 507. Preferably, the cryogen is forced through holes 510, on the surface of hollow tip 505 and of annular cooling passage 507, under pressure. Holes 510 therefore preferably extend into hollow tip 505, which acts as an expansion chamber. Annular cooling passage 507 operates as previously described.

In the operation of cryoprobe 500, cryogen enters through cryogen inlet 509 to cryogen supply passage 502, and travels down cryogen supply passage 502 until it reaches hollow tip 505. The cryogen then expands and cools tip 505. As shown, tip 505 optionally features an additional solid tip 530 over hollow tip 505, which is cooled as hollow tip 505 is cooled. The expanded cryogen then returns through holes 510 to annular cooling passage 507, thereby providing additional cooling of hollow tip 505, and is exhausted through cryogen exhaust passage 303. The direction of cryogen flow is shown with arrows 506.

Preferably a cross-sectional area of the return passage 507 is about equal to a cross-sectional area of the supply passage 502, and also preferably a flow of cryogen in the cryogen supply passage 502 urges cryogen through the radial flow section into the peripheral return passage 507.

Figure 6A:
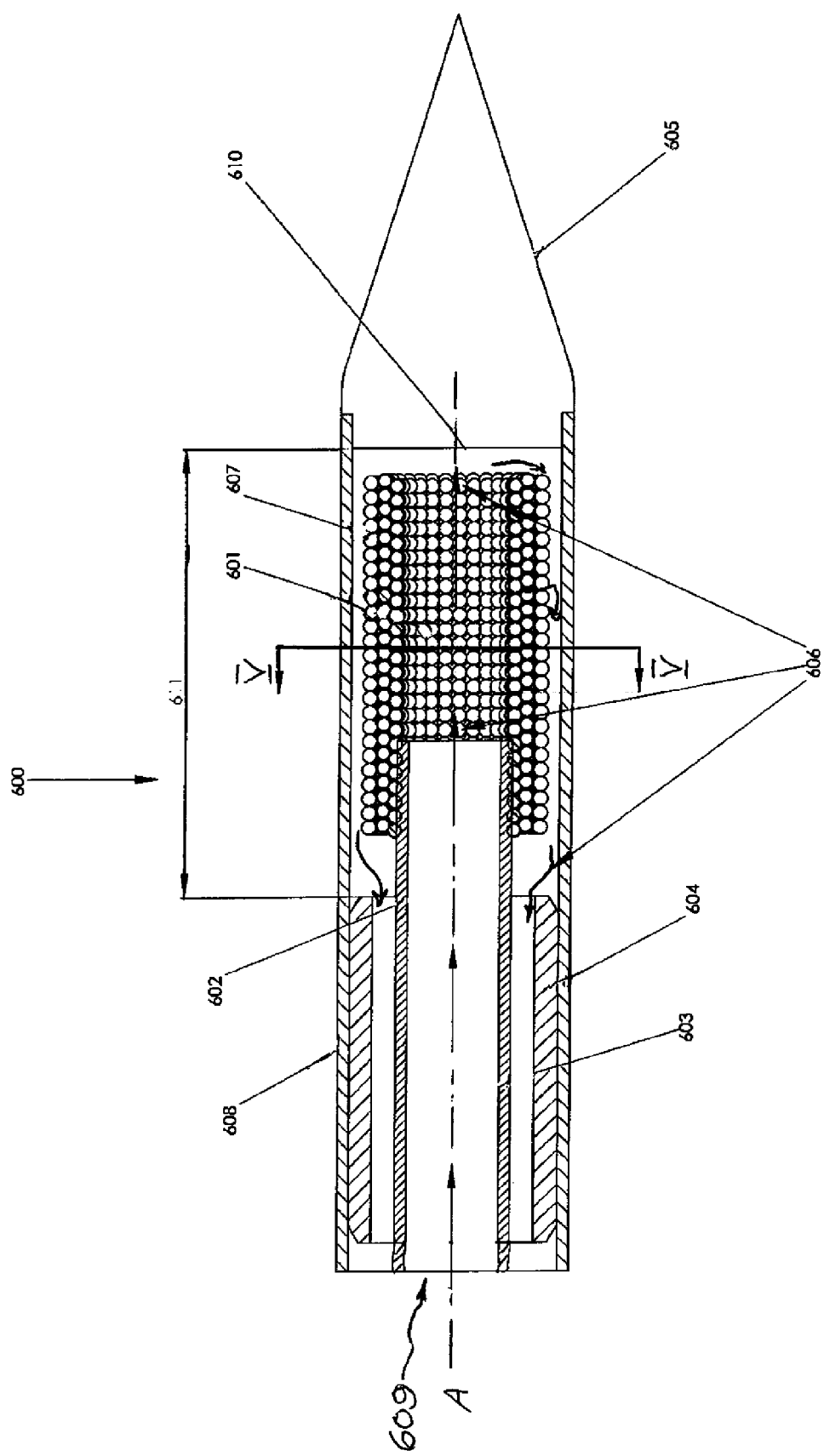
FIG. 6a is a longitudinal cross-sectional view of a cryoprobe consistent with an embodiment of the present invention, with an annular cooling passage provided for return flow for a closed, optionally solid, cryotip.
Figure 6B:
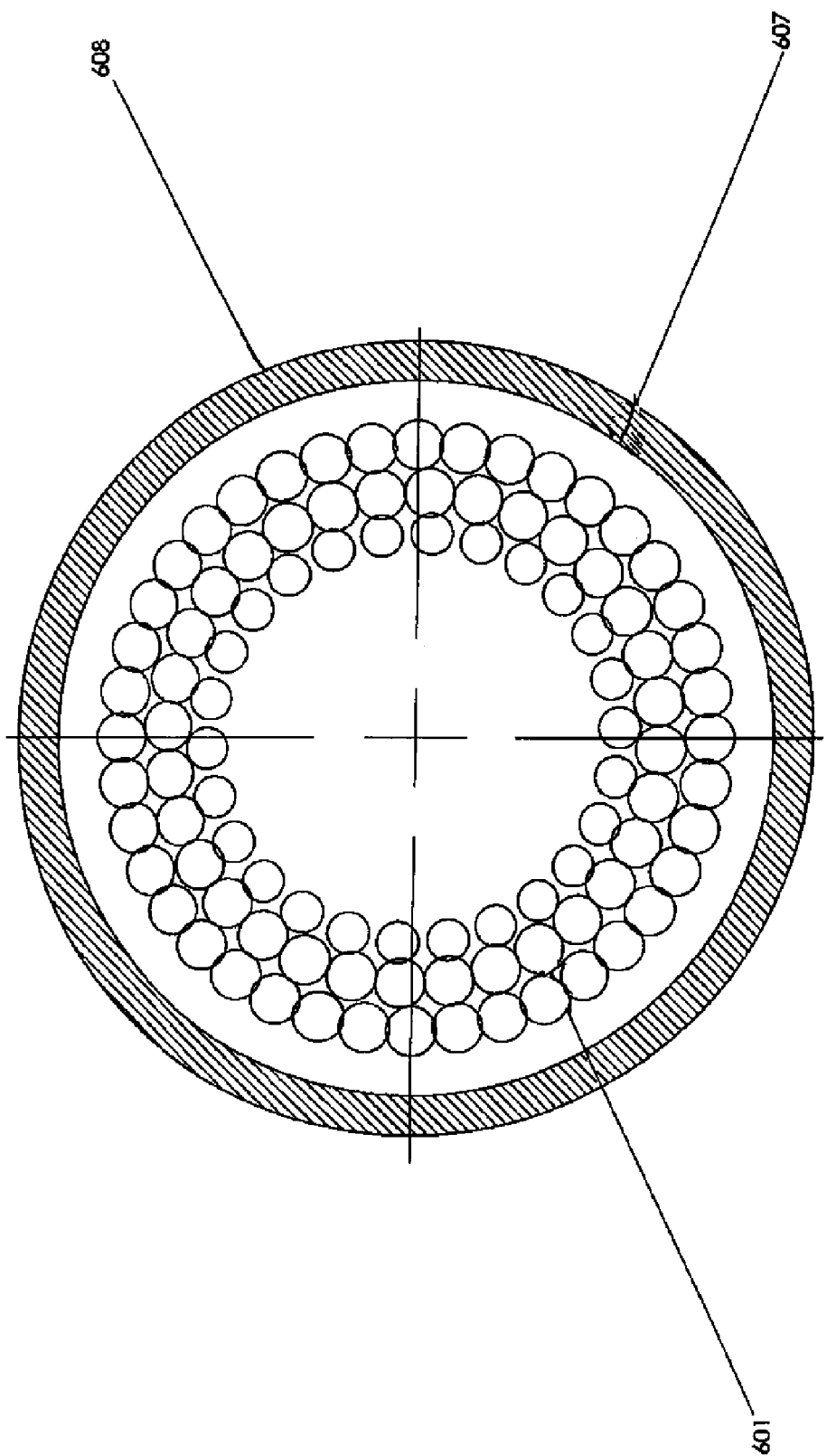

Referring to FIGS. 6a and 6b, cryoprobe 600 is similar in some aspects to cryoprobe 100, in that a reflecting surface 610 closes off tip 605, which may optionally be solid. Reflecting surface 610 preferably acts as a flow deflector between tip 605 and supply passage 602, and is fixedly and spacedly disposed from supply passage 602. Cryogen and is forced through annular cooling passage 607, which preferably features a plurality of radial throughholes 631 in the radial flow section. Such radial throughholes 631 increase the space for boiling of the cryogen, such that the cryogen cools tip 605 through cooling reflecting surface 610 and radial throughholes 631 in return passage 607.

Figure 7:
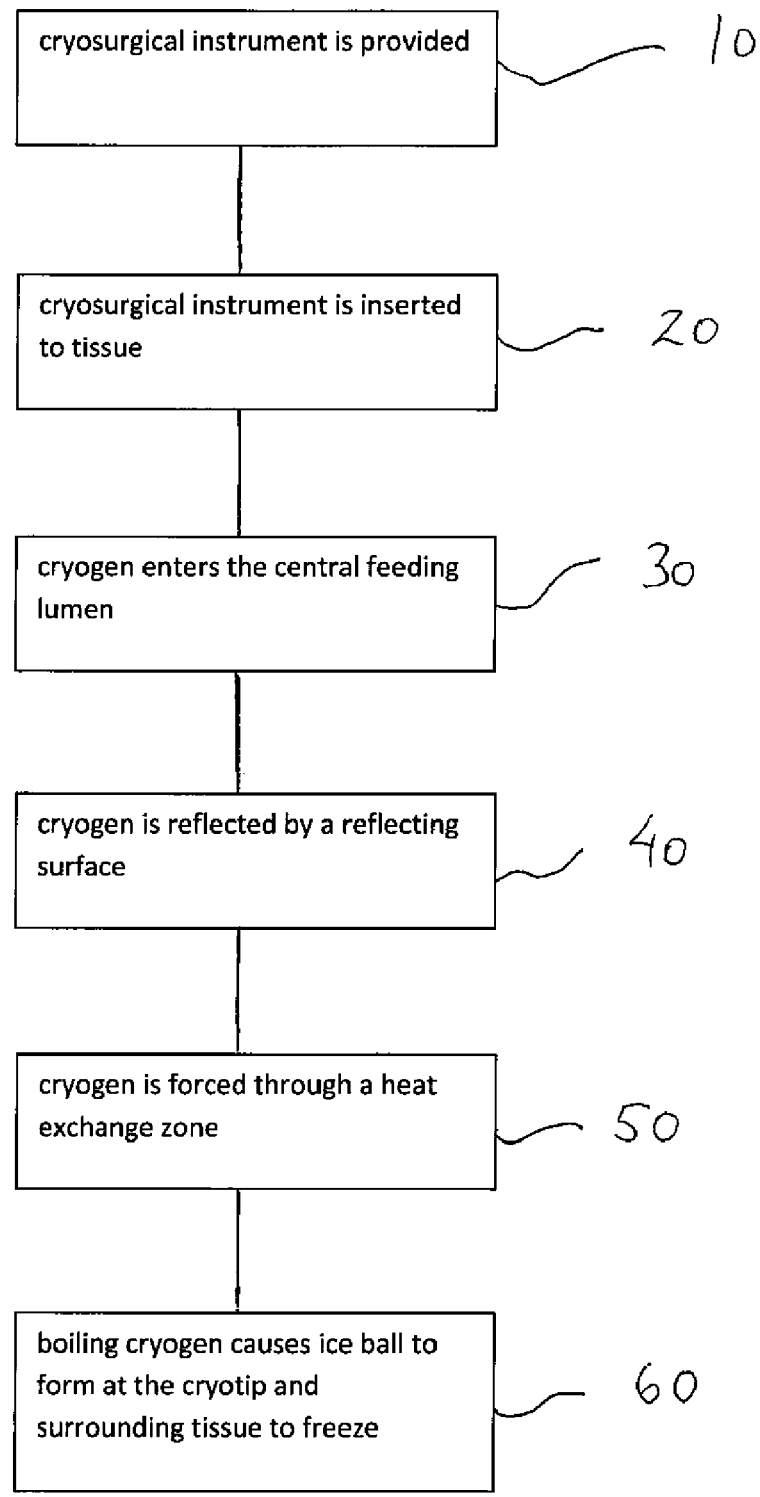
FIGS. 7 and 8 are flowcharts, illustrating respective exemplary methods of treatment each of which is consistent with embodiment of the present invention.

FIG. 7 is a flowchart illustrating a method of treatment with a cryosurgical instrument consistent with an embodiment of the present invention. The cryosurgical instrument may be, by way of non-limiting examples, any of the cryoprobes 100, 300, 400, and 600.

In operation 10, a cryosurgical instrument is provided. In operation 20, the cryosurgical instrument is inserted to the tissue to be treated. In operation 30, cryogen enters the cryogen supply passage. In operation 40, the cryogen is reflected by a reflecting surface, which closes off the tip, which may optionally be solid. In operation 50, the cryogen is forced through a heat exchange zone of the cryosurgical instrument, such that partial change of phase occurs at the reflecting surface and at the heat exchange zone. In operation 60, the boiling cryogen causes an ice ball to form at the cryotip and the surrounding tissue to freeze.

Figure 8:
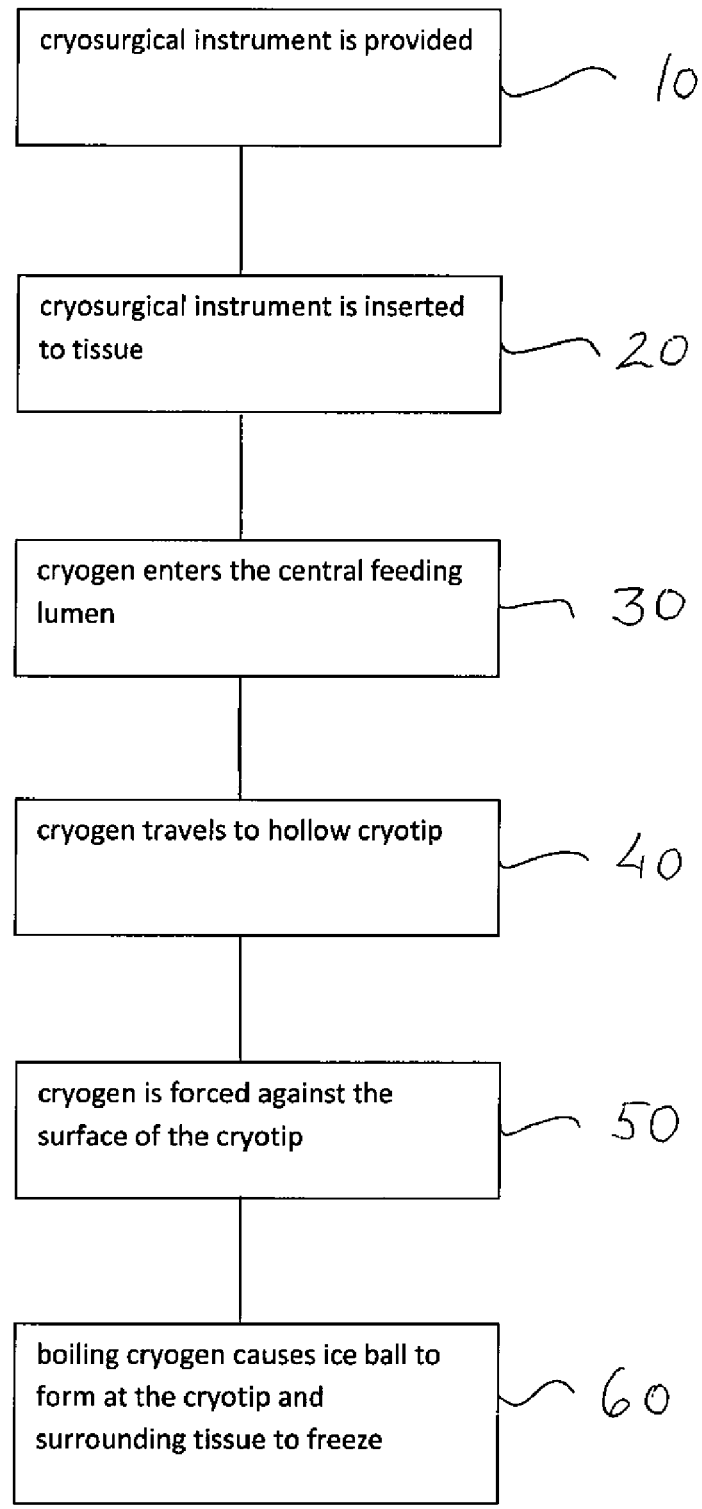

FIG. 8 is a flowchart illustrating a method of treatment with a cryosurgical instrument consistent with an embodiment of the present invention. The cryosurgical instrument may be, by way of non-limiting examples, cryoprobe 200 or 500.

In operation 10, a cryosurgical instrument is provided. In operation 20, the cryosurgical instrument is inserted to the tissue to be treated. In operation 30, cryogen enters the cryogen supply passage. In operation 40, the cryogen travels to the cryotip, which is hollow. In operation 50, the cryogen is forced against the surface of the cryotip, such that boiling occurs at the cryotip (and optionally also in a heat exchange zone of the cryosurgical device. In operation 60, the partially phase changed cryogen causes an ice ball to form at the cryotip and the surrounding tissue to freeze.

Examples of various features/aspects/components/operations have been provided to facilitate understanding of the disclosed embodiments of the present invention. In addition, various preferences have been discussed to facilitate understanding of the disclosed embodiments of the present invention. It is to be understood that all examples and preferences disclosed herein are intended to be non-limiting.

Although selected embodiments of the present invention have been shown and described individually, it is to be understood that at least aspects of the described embodiments may be combined.

Also although selected embodiments of the present invention have been shown and described, it is to be understood the present invention is not limited to the described embodiments. Instead, it is to be appreciated that changes may be made to these embodiments without departing from the principles and spirit of the invention, the scope of which is defined by the claims and the equivalents thereof.

What is claimed is:

1. A cryosurgical instrument comprising:

a tubular housing having a longitudinal axis, a proximal end, and a tip at a distal end;

a cryogen supply passage extending from the proximal end to the distal end along the longitudinal axis, the supply passage having an upstream portion proximate to the proximal end and a downstream portion proximate to the distal end;

a heat exchange enhancing member in the housing, disposed along the longitudinal axis, and surrounding at least some of the downstream portion of the supply passage, the enhancing member having a plurality of return channels circumferentially disposed about the longitudinal axis and extending longitudinally through the enhancing member; and a flow deflector between the tip and the supply passage, the flow director adapted and configured to deflect a cryogen flow exiting from the supply passage to the return channels and to absorb heat, thereby cooling the tip, the flow director fixedly and spacedly disposed from the supply passage, wherein a flow of cryogen in the cryogen supply passage urges cryogen that has exited the cryogen supply passage to flow into the return channels, and wherein a sum of cross-sectional areas of the plurality of return channels is about equal to a cross-sectional area of the supply passage.

2. The cryosurgical instrument of claim 1, wherein the return channels are straight.

3. The cryosurgical instrument of claim 1, wherein the cryogen absorbs heat in the return channels and exhibits two-phase flow in the supply channel and the return channels.

4. The cryosurgical instrument of claim 1, wherein the plurality of return channels are disposed at a circumferential periphery of the heat exchange enhancing member and sealingly capped by an inner surface of the tubular housing.

5. The cryosurgical instrument of claim 1 wherein the plurality of return channels are disposed in the heat exchange enhancing member.

6. The cryosurgical instrument of claim 1, wherein the return channels are adjacent to a circumferential periphery of the cryogen supply passage.

* * * * *